United States Patent [19]

Wojtowicz

[11] 4,389,318

[45] Jun. 21, 1983

[54] RAPIDLY DISSOLVING MIXTURES CONTAINING TRICHLOROISOCYANURIC ACID

[75] Inventor: John A. Wojtowicz, Cheshire, Conn.

[73] Assignee: Olin Corporation, New Haven, Conn.

[21] Appl. No.: 248,133

[22] Filed: Mar. 30, 1981

[51] Int. Cl.$^3$ ............................................. C02F 1/76
[52] U.S. Cl. ..................................... 210/755; 71/67; 210/764; 252/187.34; 424/44; 424/149
[58] Field of Search ............... 210/755, 764; 252/176, 252/350, 187.34; 424/44, 149; 71/67; 422/37

[56] References Cited

U.S. PATENT DOCUMENTS

| | | | |
|---|---|---|---|
| 2,607,738 | 8/1952 | Hardy | 252/99 |
| 2,980,622 | 4/1961 | Symes | 252/99 |
| 3,165,521 | 1/1965 | Slezak et al. | 210/755 |
| 3,236,726 | 2/1966 | Ross | 424/149 |
| 3,293,188 | 12/1966 | Brown et al. | 424/149 |
| 3,296,069 | 1/1967 | Kowalski | 210/755 |
| 3,873,685 | 3/1975 | Kibbel et al. | 424/149 |
| 3,898,223 | 8/1975 | Wojtowicz | 252/187 C |
| 4,025,628 | 5/1977 | Dewey et al. | 424/44 |

*Primary Examiner*—Peter A. Hruskoci
*Attorney, Agent, or Firm*—James B. Haglind; Donald F. Clements

[57] ABSTRACT

A composition suitable for sanitizing water bodies consists of a mixture in compressed form of trichloroisocyanuric acid and an alkali metal bicarbonate. The mixture has a molar ratio of alkali metal bicarbonate to trichloroisocyanuric acid of from about 3:1 to about 1:1 and a moisture content of less than 0.2 percent by weight of the mixture.

The novel compositions, for example in tablet form, rapidly dissolve in water bodies such as swimming pools, spas and hot tubs to provide high concentrations of available chlorine for sanitizing the water. The compositions effervesce during dissolution and are resistant to thermal decomposition.

11 Claims, No Drawings

RAPIDLY DISSOLVING MIXTURES CONTAINING TRICHLOROISOCYANURIC ACID

This invention is related to compositions for sanitizing water bodies. More particularly, this invention is related to mixtures containing trichloroisocyanuric acid for sanitizing water bodies.

Trichloroisocyanuric acid is a known compound for sanitizing water bodies such as swimming pools by the formation of available chlorine when dissolved in the water. The solubility rate of trichloroisocyanuric acid is, however, low and trichloroisocyanuric acid is unsuitable where a rapidly dissolving source of available chlorine is required.

When increased solubility in water is required, other chloroisocyanurates such as dichloroisocyanuric acid or alkali metal salts of dichloroisocyanuric acid and their hydrates are employed. One method of producing sodium dichloroisocyanurate or potassium dichloroisocyanurate is described in U.S. Pat. No. 3,035,057 issued May 15, 1962, to W. F. Symes. In this method, trichloroisocyanuric acid is reacted with trisodium isocyanurate or tripotassium isocyanurate in an aqueous medium maintained at a pH of 5.0 to 7.5 at a temperature in the range of 0° to 50° C. Following filtering and drying, the desired alkali metal dichloroisocyanurate or its hydrate is recovered.

Also employed as sanitizing agents are dry mixtures of trichloroisocyanuric acid with alkali metal salts such as alkali metal phosphates including trisodium phosphate and tetrasodium phosphate as well as sodium carbonate, sodium borate, and sodium silicate where the amount of trichloroisocyanuric acid is in the range of 0.5 percent to 90 percent by weight.

Stabilized trichloroisocyanuric acid compositions suitable as sanitizing agents have been prepared from mixtures of trichloroisocyanuric acid, cyanuric acid, water-soluble alkali metal salts, and moisture. The composition generally contains from 0.5 to 40 percent by weight of trichloroisocyanuric acid, 0.1 to 1 mole of cyanuric acid per mole of trichloroisocyanuric acid, 0.5 to 5 percent by weight of water as moisture and the remainder as water-soluble alkali metal salt or salts. Water-soluble alkali metal salts which may be used include trialkali metal phosphates, dialkali metal hydrogen phosphates, alkali metal pyrophosphates, water-soluble alkali metal silicates, water-soluble alkali metal borates and water-soluble alkali metal carbonates or bicarbonates. These mixtures have a maximum available chlorine concentration of 36.6 percent, with the preferred available chlorine concentration being in the range of 2.25 to 13.75 percent available chlorine.

There is a need for rapidly dissolving compositions containing trichloroisocyanuric acid having high available chlorine concentrations for use in sanitizing water bodies.

It is an object of the present invention to provide compositions for sanitizing water bodies containing trichloroisocyanuric acid which dissolves rapidly in water.

Another object of the present invention is to provide compositions containing trichloroisocyanuric acid which provide high concentrations of available chlorine for sanitizing water bodies.

An additional object of the present invention is to provide a method for sanitizing water bodies employing a rapidly dissolving composition containing trichloroisocyanuric acid.

These and other objects of the invention are accomplished in a composition in compressed form for sanitizing water bodies which consists of a mixture of trichloroisocyanuric acid and an alkali metal bicarbonate, the mixture having a molar ratio of the alkali metal bicarbonate to the trichloroisocyanuric acid of from about 3:1 to about 1:1, and having a moisture content of less than about 0.2 percent by weight of the mixture.

The novel compositions of the present invention include trichloroisocyanuric acid (TCCA) which is a commercially available compound having an available chlorine concentration in the range of from about 89 to about 91.5 percent. Trichloroisocyanuric acid is produced by known processes such as those described, for example, in U.S. Pat. Nos. 3,757,018, issued Sept. 4, 1973, to R. N Mesiah; 3,810,982, issued May 14, 1974, to R. N. Mesiah; 3,835,134, issued Sept. 10, 1974, to H. W. Schiessl et al; and 3,835,135, issued Sept. 10, 1974, to D. L. Sawhill. When placed in a water body such as a swimming pool, trichloroisocyanuric acid dissolves slowly to release its available chlorine concentration and sanitize the water body. The solubility rate, for example, for tablets containing 5 grams of trichloroisocyanuric acid in water at 25° C. is about 0.1 gram per hour.

The second required ingredient of the novel composition is an alkali metal bicarbonate. Suitable alkali metal bicarbonates include sodium bicarbonate and potassium bicarbonate, with sodium bicarbonate being preferred. As alkali metal bicarbonates readily react with TCCA in the presence of moisture, it is necessary that the mixture of trichloroisocyanuric acid and alkali metal bicarbonate be substantially anhydrous, that is the mixture should have a moisture content of less than about 0.2 percent and preferably less than 0.1 percent by weight of the mixture. By maintaining the mixture substantially anhydrous, the mixture can be packaged in air tight, humectantly sealed packaging which prevents atmospheric moisture from coming in contact with the product.

Suitable particle sizes for the TCCA and the alkali metal bicarbonate employed in the compositions of the present invention include those in the range of from about 40 to about 150 microns, preferably from about 50 to about 100 microns.

The novel compositions of the present invention are supplied in compressed forms such as, for example, tablets, rings, discs, sticks, briquets, etc. in which a homogeneous mixture of the components is provided. Preferred embodiments of the compressed forms are tablets, discs, and briquets with tablets being particularly preferred.

When the novel composition in compressed form is added to a water body such as a swimming pool, spa, or hot tub, a reaction between the trichloroisocyanuric acid and the alkali metal bicarbonate takes place which is believed to be expressed by the following equation in which sodium bicarbonate is the alkali metal bicarbonate:

$$Cl_3C_3N_3O_3 + NaHCO_3 \rightarrow NaCl_2C_3N_3O_3 + CO_2 + HOCl \qquad (1)$$

That is, sodium dichloroisocyanurate is produced in situ. The reaction takes place rapidly and the sodium dichloroisocyanurate and hypochlorous acid formed readily release their available chlorine contents. The novel compositions consisting of trichloroisocyanuric acid and anhydrous alkali metal bicarbonate having a mole ratio of alkali metal bicarbonate to TCCA of from about 3:1 to about 1:1 have available chlorine concentrations in the range of about 45 percent to about 67 percent.

To prevent the release of the hypochlorous acid generated from the water body, in a preferred embodiment, cyanuric acid is added to the mixture. The presence of cyanuric acid in the mixture is believed to provide additional alkali metal dichloroisocyanurate when the mixture is added to water, as expressed in the following equation in which sodium bicarbonate is the alkali metal bicarbonate:

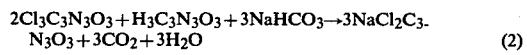

$$2Cl_3C_3N_3O_3 + H_3C_3N_3O_3 + 3NaHCO_3 \rightarrow 3NaCl_2C_3N_3O_3 + 3CO_2 + 3H_2O \quad (2)$$

Novel compositions of the present invention containing TCCA, an alkali metal bicarbonate, and cyanuric acid and which have available chlorine concentrations in the range of about 45 to about 67 percent contain at least about 50 percent by weight of TCCA. Mole ratios of cyanuric acid to TCCA in the compositions are in the range of from about 0.05:1 to about 0.75:1 and preferably from 0.25:1 to about 0.50:1.

To provide suitable dissolving rates, compositions consisting of mixtures of trichloroisocyanuric acid, cyanuric acid and an alkali metal bicarbonate preferably include mole ratios of the alkali metal bicarbonate to trichloroisocyanuric acid in the range of from about 3:1 to about 1.5:1.

To the user, the addition of a compressed form having controlled amounts of the novel compositions of the present invention is advantageous. As shown by equations (1) and (2) above, carbon dioxide gas is released during the reaction. This gas release continues until the reaction is complete and the water in the water body has received sanitizing amounts of available chlorine. This visual confirmation of sanitizing action is not provided by other compositions such as those containing mixtures of trichloroisocyanuric acid and alkali metal carbonates as the solubility rates of these mixtures is considerably lower and significant amounts of effervescence are not readily seen by the user.

Compressing the novel compositions of the present invention, for example by tabletting, can be accomplished without the addition of a binding agent or a release agent.

In an alternate embodiment, dichloroisocyanuric acid may be employed in the compositions of the present invention. When added, for example, to a mixture of trichloroisocyanuric acid and an alkali metal bicarbonate, the amount of dichloroisocyanuric acid used should maintain the available chlorine concentration at above about 45 percent.

The novel compositions of the present invention may contain additional ingredients such as algaecides which are commonly employed in the treatment of water bodies. Suitable algaecides which can be incorporated in the compositions include, for example, quaternary ammonium compounds, bis(ethylamino-)chloro-s-triazine, halogenated quinones, sodium chlorate, carbamates, polyoxyethylene-dimethyliminoethylene-dimethyliminoethylene dichloride, and copper chelates with ethylene diamine tetracetic acid (EDTA), triethanolamine (TEA), gluconic acid, or citric acid.

These additives are present in amounts which are sufficient to provide the desired result, but insufficient to reduce the available chlorine concentrations of the compositions to lower than about 45 percent. As the novel compositions of the present invention are substantially anhydrous and non-hygroscopic, they are compatible with additives such as those cited above with a minimal risk of a chemical interaction. Sodium dichloroisocyanurate and its hydrates, however, are hygroscopic and contain sufficient moisture so that these additives are less compatible and their incorporation results in a greater risk of chemical interaction.

The novel compositions of the present invention in compressed form are particularly useful in sanitizing water bodies having water at temperatures suitable for bathing or swimming, for example, temperatures in the range of from about 12° to about 43° C., preferably from about 20° to about 43° C., and more preferably from about 35° to about 41° C. Examples of these more preferred water bodies include spa baths, commonly called spas and hot tubs. Compressed forms, such as tablets, when added to water bodies at these elevated temperatures have a dissolving time in the range of from about 0.02 to about 2 minutes per gram of the novel composition.

Compositions of the present invention have solubility rates comparable to those of alkali metal dichlorocyanurates and their hydrates without requiring the added costs encountered in manufacturing these salts.

In contrast to the alkali metal dichloroisocyanurates or their hydrates, the novel compositions of the present invention, in granular or compressed form, do not undergo sustained thermal decomposition when contacted, for example, with a burning match or a lighted cigarette. Thus these compositions are safe to ship, store, and be used by the general public with a minimal risk of damage or injury due to thermal decomposition.

The novel compositions of the present invention which are suitably used in sanitizing water bodies are further illustrated by the following examples. All percentages are by weight unless otherwise specified.

EXAMPLE 1

A homogeneous mixture of trichloroisocyanuric, anhydrous sodium bicarbonate and cyanuric acid was prepared. The mixture contained amounts of ingredients which provided molar ratios of 1.5 moles of anhydrous NaHCO₃ per mole of anhydrous trichloroisocyanuric acid, 0.5 mole of cyanuric acid per mole of trichloroisocyanuric acid and less than 0.1 percent by weight of moisture. Tablets, each containing 5 grams of the mixture, were prepared by compressing the mixture in a tabletting machine operated at a pressure of 5,000 lbs. per square inch. The dissolving rate of the tablets was determined by adding a tablet to a container having 200 milliliters of distilled water at a temperature of 25° C. During the dissolution period, the solution was stirred. As the tablet dissolved considerable effervescence occurred. After 8.5 minutes, effervescence ceased and the tablet was totally dissolved.

COMPARATIVE EXAMPLE A

Tablets of sodium dichloroisocyanurate dihydrate, each tablet containing 5 grams, were prepared and the dissolving rate of the tablets were determined using the apparatus and method of EXAMPLE 1. The sodium dichloroisocyanurate tablet was totally dissolved after 8.5 minutes. During the dissolution period, there was no evidence of effervescence.

Tablets of the novel composition of the present invention had identical dissolving rates in water, as shown in EXAMPLE 1, to tablets of sodium dichloroisocyanurate dihydrate employed in COMPARATIVE EXAMPLE A. In addition, the considerable amount of effervescence provided visual evidence of the length and termination of the dissolving period.

EXAMPLE 2

Using the mixture of trichloroisocyanuric acid, anhydrous sodium bicarbonate and cyanuric acid of EXAMPLE 1, tablets containing 25 grams of the mixture were prepared in a tabletting machine at a pressure of 2500 psi. The tablets were cylindrical, having a diameter of 1.5 inches and a thickness of 0.5 inch. The dissolving rate of the tablets was determined by adding a tablet to a container having 200 milliliters of distilled water at temperatures of 25° C. and 40° C. The solution was stirred during the dissolution period and copious effervescence was noted. The dissolving times were as follows:

At 25° C.—15 minutes
At 40° C.—2.5 minutes

EXAMPLE 3

A dry mixture of cyanuric acid (CA), sodium bicarbonate, and trichloroisocyanuric acid (TCCA) was prepared having molar ratios of 0.5 mole of cyanuric acid and 1.5 moles of $NaHCO_3$ per mole of trichloroisocyanuric acid. The mixture had a moisture content of less than 0.1 percent by weight. A portion of the mixture was added to each of two septum vials. To one of the vials, water was added in an amount of 0.5 percent by weight of the mixture. The vials were sealed and placed in an oven maintained at a temperature of 60° C. for a period of 1.5 hours. At the end of this period, the head gases in each vial were analyzed by gas chromatography. The results were as follows:

| TCCA—$NaHCO_3$—CA Formulation | | |
|---|---|---|
| | Dry | 0.5% $H_2O$ |
| % Air | 97.3 | 22.2 |
| % $CO_2$ | 2.7 | 77.8 |
| Pressure | slight | very high |

The gas analysis results show that in the presence of a relatively small amount of water, a considerable amount of the $NaHCO_3$ decomposes to produce $CO_2$ gas. $CO_2$ gas is generated in sufficient amounts to bulge humectantly sealed plastic packaging to the rupture point.

What is claimed is:

1. A composition in compressed form for sanitizing water bodies consisting essentially of a mixture of trichloroisocyanuric acid and an alkali metal bicarbonate, said mixture having a molar ratio of said alkali metal bicarbonate to said trichloroisocyanuric acid of from about 3:1 to about 1:1, an available chlorine concentration in the range of from about 45 to about 67 percent, and having a moisture content of less than about 0.2 percent by weight of the mixture.

2. A composition for sanitizing water bodies which consists of a mixture of trichloroisocyanuric acid and an alkali metal bicarbonate, said mixture having a molar ratio of said alkali metal bicarbonate to said trichloroisocyanuric acid of from about 3:1 to about 1:1, an available chlorine concentration in the range of from about 45 to about 67 percent, and said mixture having a moisture content of less than about 0.2 percent by weight of the mixture.

3. The composition of claim 1 or 2 in which said alkali metal bicarbonate is sodium bicarbonate.

4. The composition of claim 1 in which said compressed form is selected from the group consisting of tablets, discs, sticks, and briquets.

5. The composition of claim 4 in which said mixture contains an algaecide.

6. A method for producing an aqueous solution of an alkali metal dichloroisocyanurate which comprises:
   (a) admixing dry trichloroisocyanuric acid and a dry alkali metal bicarbonate to form a homogeneous mixture having a molar ratio of said alkali metal bicarbonate to said trichloroiso-cyanuric acid of from about 3:1 to about 1:1; said mixture having a moisture content of less than about 0.2 percent by weight of said mixture and an available chlorine concentration in the range of from about 45 to about 67 percent,
   (b) compressing said mixture to produce a compressed form of said mixture, and
   (c) feeding said compressed form of said mixture to a water body to produce in situ said aqueous solution of an alkali metal dichloroisocyanurate.

7. The method of claim 6 in which in step (a) cyanuric acid is incorporated in the mixture in an amount which provides said mixture with from about 0.25 to about 0.50 mole of said cyanuric acid per mole of trichloroisocyanuric acid.

8. A composition in compressed form for sanitizing water bodies consisting essentially of a mixture of trichloroisocyanuric acid, an alkali metal bicarbonate and cyanuric acid said mixture having a molar ratio of said alkali metal bicarbonate to said trichloroisocyanuric acid of from about 3:1 to about 1:1, a mole ratio of said cyanuric acid to said trichloroisocyanuric acid in the range of from about 0.05:1 to about 0.75:1, said mixtures containing at least about 50 percent by weight of said trichloroisocyanuric acid, and having a moisture content of less than about 0.2 percent by weight of the mixture.

9. The composition of claim 1 or claim 8 in which said compressed form is a tablet having a dissolving time in water at a temperature of from about 20° C. to about 43° C. of from about 0.02 to about 2 minutes per gram.

10. A method of sanitizing a water body having a temperature in the range of from about 12° to about 43° C. which comprises adding to said water body the composition of claim 8.

11. The method of claim 10 or 6 in which said water body is selected from the group consisting of swimming pools, spas and hot tubs.

* * * * *